(12) United States Patent
Bondarev

(10) Patent No.: US 9,078,901 B2
(45) Date of Patent: *Jul. 14, 2015

(54) PHARMACOLOGICAL MODULATION OF TELOMERE LENGTH IN CANCER CELLS FOR PREVENTION AND TREATMENT OF CANCER

(71) Applicant: ALT Solutions Inc., Wilmington (DE)

(72) Inventor: Igor E. Bondarev, St. Petersburg (RU)

(73) Assignee: ALT Solutions Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,752

(22) Filed: Dec. 12, 2013

(65) Prior Publication Data

US 2014/0113918 A1    Apr. 24, 2014

Related U.S. Application Data

(63) Continuation of application No. 11/920,668, filed on Nov. 19, 2007, now Pat. No. 8,609,623.

(51) Int. Cl.

| | |
|---|---|
| *A61K 31/70* | (2006.01) |
| *A01N 43/04* | (2006.01) |
| *A61K 31/522* | (2006.01) |
| *A61K 45/06* | (2006.01) |
| *A61N 5/10* | (2006.01) |
| *A61K 9/00* | (2006.01) |

(52) U.S. Cl.
CPC ............. *A61K 31/522* (2013.01); *A61K 9/0095* (2013.01); *A61K 45/06* (2013.01); *A61N 5/10* (2013.01); *A61K 9/0019* (2013.01)

(58) Field of Classification Search
CPC ........ C07H 19/20; C07H 19/10; C07H 21/00; A61K 31/70; A61K 31/7076; A61K 31/185; A61K 31/12; C07D 413/04; C07D 401/12; C07D 413/14; C07D 231/12; C07D 249/08; A01N 41/04; C07C 49/84; C07C 309/46
USPC ........................................ 514/49, 263.36, 45
See application file for complete search history.

(56) References Cited

U.S. PATENT DOCUMENTS

| | | | |
|---|---|---|---|
| 5,585,363 A | 12/1996 | Scanlon et al. | |
| 5,631,236 A | 5/1997 | Woo et al. | |
| 5,683,990 A | 11/1997 | Rideout et al. | |
| 6,066,624 A | 5/2000 | Woo et al. | |
| 2003/0031681 A1 | 2/2003 | McCart et al. | |
| 2003/0211163 A1 | 11/2003 | Chong | |

FOREIGN PATENT DOCUMENTS

| | | |
|---|---|---|
| WO | WO 96/40166 A1 | 12/1996 |
| WO | WO 00/78941 A2 | 12/2000 |

OTHER PUBLICATIONS

Sporn et al. Am J Med. Jun. 1981;70(6):1231-5.*
Hannemann et al., Nephrotoxicity of acyclovir and *cis*-diamminedichloroplatinum (II)—effect of co-administration in rats. J. Cancer Res. Clin. Oncol. 1992, vol. 118, pp. 181-186.
International Search Report issued Jul. 1, 2008 in International Application No. PCT/US06/19488 (1 page).
Chabner et al., 2005, Nature Reviews Cancer 65-72.
Bocchetta et al., 2004, Oncogene 23:6484-6491.
Han et al., (pharmaceutical research) 15(8); 1154-1159 (1998).
John Hopkins University (2001), 3 pages.
US Dept. of Health and Human Services at the National Cancer Institute as recent as May 18, 2008.
Stella et al., (Prodrugs: Challenges and Rewards, Part 1, 2007) 677-694.
Supplementary European Search Report, from the European Patent Office, in corresponding European Patent Application No. 06 77 0683, dated Jun. 26, 2012, pp. 1-4.
B. Hladon et al., "In Vitro Cytostatic Activity of 8-Substituted and Tricyclic Analogues of Acyclovir," Polish Journal of Pharmacology, Jan. 1, 2002, vol. 54, No. 1, pp. 45-53.
D.W. Siegmann-Louda et al., "Ability of Organotin Polymers Containing Acyclovir to Inhibit Balb 3T3 Cells," Polymeric Materials: Science & Engineering, Jan. 1, 2004, vol. 90, pp. 512-514.
Valeriánováet al., "Antitumour Activity of $N^6$—Substituted PMEDAP Derivatives Against T-Cell Lymphoma," Anticancer Research, May 1, 2001, vol. 21, No. 3B, pp. 2057-2064.
N. Margiotta et al., "Antiviral Properties and Cytotoxic Activity of Platinum(II) Complexes with 1,10-Phenanthrolines and Acyclovir of Penciclovir," Journal of Inorganic Biochemistry, Jan. 1, 2004, vol. 98, No. 8, pp. 1385-1390.
M. Hájek et al., "Inhibition of Human Telomerase by Diphosphates of Acyclic Nucleoside Phosphonates," Biochemical Pharmacology, Sep. 15, 2005, vol. 70, No. 6, pp. 894-900.
H. Xiang-Liang et al., "Study of ACV Treatment of Subcutaneous Tumors Induced with Inoculation of Pulmonary Adenocarcinoma Cells A549-TK in Nude Mice," Disan-Junyi-Daxue-Xuebao: Shuangyuekan=ACTA Academiae Medicinae Militaris Tertiae, Chongqing, CN, Aug. 2000, vol. 22, No. 8, pp. 766-768.
Office Action from Japanese Patent Office for corresponding Japanese Patent Application No. 2008-512547 mailed Jan. 29, 2013.
Boguslaw Hladon et al, "In Vitro Cytostatic Activity of 8-Substituted and Tricyclic analogues of Acyclovir", Polish Journal of Pharmacology, (2002), pp. 45-53.
Office Action from European Patent Office of corresponding European Application No. 06 770 683.8 dated May 14, 2013.
Morris J. Robins et al., "Nucleic Acid Related Compounds. 47. Synthesis and Biological Activities of Pyrimidine and Purine "Acyclic" Nucleoside Analogues", J. Med. Chem, 1984, 27, pp. 1486-1492.

* cited by examiner

*Primary Examiner* — Shirley V Gembeh

(74) *Attorney, Agent, or Firm* — Juan Carlos A. Marquez; Bacon & Thomas PLLC

(57) ABSTRACT

Acyclic nucleoside analogs such as acyclovir, ganciclovir, penciclovir and the corresponding pro-drugs, i.e., valacyclovir, valganciclovir and famciclovir, respectively have been identified as inhibitors or antagonists of both telomerase (encoded by TERT) and reverse transcriptase encoded by L-1 (LINE-1) RT, and as useful for treating or preventing cancers induced or mediated by the two enzymes. Method of treating or preventing such cancers in patients involves administration of a therapeutically effective amount of a composition having an inhibitor or antagonist of the reverse transcriptases in cells of the patients. The inhibitor or antagonist blocks lengthening of telomeres in telomerase positive and telomerase negative cells. Methods and kits for detecting pathologically proliferating cells expressing TERT and L1RT are also disclosed.

20 Claims, 3 Drawing Sheets

PHARMACOLOGICAL MODULATION OF TELOMERE LENGTH IN CANCER CELLS FOR PREVENTION AND TREATMENT OF CANCER

This application is a Continuation of U.S. Application Ser. No. 11/920,668, filed on Nov. 19, 2007. Priority is claimed based U.S. application Ser. No. 11/920,668, filed on Nov. 19, 2007, which claims the priority of national stage application PCT/US2006/019488, filed on May 18, 2006, which claims priority from U.S. Provisional Application No. 60/682,110 filed May 18, 2005, and the text of application 60/682,110 is incorporated by reference in its entirety herewith.

FIELD OF THE INVENTION

The present invention is directed to the field of cancer therapy. Specifically, the present invention relates to the regulation of telomere elongation in cancer cells. More particularly, the present invention relates to the use of acyclic nucleoside analogs for treating or preventing cancers.

BACKGROUND OF THE INVENTION

An asymmetry in the synthesis of leading and lagging DNA strands creates the "end problem" for replication of linear genomes.[1] To overcome this problem, eukaryotic chromosomes have specialized end structures, telomeres, consisting of TTAGGG repeats.[2] Telomerase[3,4] is a ribonucleoprotein enzyme that elongates telomeres and therefore maintains chromosomal stability in majority of cancer cells during cell doubling[5]. The gradual loss of DNA from the ends of telomeres during cell doubling has been implicated in the control of cellular proliferative potential in somatic cells[6].

Normal cultured human cells have a limited replication potential in culture. Normal cells in culture replicate until they reach a discrete point at which population growth ceases. This is termed mortality stage 1 (M1 stage) and is caused by the shortening of a few telomeres to a size that leads to a growth arrest called cellular senescence. This stage can be bypassed by abrogation of the function of p53 and pRB human tumor suppressor genes. The cells then can continue to proliferate with further decreases in telomere length until another check point termed mortality stage 2 (M2 stage) or crisis stage. The growth arrest in the M2 stage is caused by balance between the cell proliferation and cell death rate. At this stage, when most of the telomeres are extremely short, end-to-end fusions and chromosomal breakage-fusion cause marked chromosomal abnormalities and apoptosis. Under rare circumstances, a cell can escape M2 and become immortal by stabilizing the length of its telomeres. This occurs through the activation of the enzyme telomerase or an alternative mechanism of telomere lengthening (i.e., alternative lengthening of telomeres or ALT).[7,8]

Human germline[9] and the majority of cancer cells[3] express telomerase. Elongation of shortened telomeres by telomerase is a major mechanism of telomere maintenance in the human cancer cells.[10] Inhibition of telomerase limits the growth of human telomerase positive cancer cells[11] by decreasing telomere length.

The use of nucleoside analogs (e.g., AZT) has been attempted to interfere with human telomerase activity with an aim to treat cancers. The methods disclosed in the prior art administering nucleoside analogs to modify telomerase activity, however, are not satisfactory or are not suitable in a clinical setting because their clinical utility is limited by a low therapeutic ratio, i.e., the ratio of toxic dose to effective dose. Further, because proliferative ability of cells including cancer cells is due to the activation of telomerase mediated telomere lengthening mechanism and/or ALT mechanism, the ideal nucleoside analogs for controlling cell proliferation would be those that are effective against both the mechanisms with minimal or no toxicity against normal cells and tissues. Thus, there is need for the identification of therapeutic nucleoside analogs that can inhibit proliferating cells such as cancer cells maintaining their telomeres either by telomerase and/or ALT mechanism.

SUMMARY OF THE INVENTION

The present invention provides methods and compositions involving the use of antiviral nucleoside analogs for modulation, suppression or inhibition of lengthening of telomeres in cells without regard to the telomere lengthening mechanism (telomerase or ALT mechanism). The present invention also discloses methods for prevention and/or treatment of proliferative disorders and all types of cancers using specific nucleoside analogs. More particularly, the present invention discloses that acyclic nucleoside analogs that can interfere with telomerase activity and L-1 (LINE-1) retrotransposon encoded reverse transcriptase (L1RT) activity in proliferating cells including cancer cells (e.g., human cancer cells) at levels that are not cytotoxic to the corresponding normal somatic cells. The present invention discloses how to use acyclic nucleoside analogs as antineoplastic or anticancer agents. In an aspect of the invention, it has been found that treatment of telomerase positive or telomerase negative cells (but having L1RT activity) with ganciclovir, acyclovir and/or penciclovir induces progressive telomere loss, G2 phase arrest, chromosomal abnormalities and eventual cell death. Further, these antineoplastic nucleoside analogs have a surprising effect on telomerase or L1RT in that clinically acceptable levels are sufficient to control telomerase activity and induce cell death in proliferating cells thereby allowing treatment or prevention of all types of cancers.

Currently, there are no therapeutic compositions in use that are based on nucleoside analogs that are acyclic, anti-telomerase, anti-L1RT and antineoplastic. Applicant is the first to provide a disclosure indicating that inhibition of telomere elongation in vivo using acyclic nucleoside analogs (also referred to herein as inhibitors or antagonists of telomere elongation) is therapeutically beneficial. Further, prior to the present invention, there was no consensus by those in the art that one could predict that such manipulations would have therapeutic utility.

As telomeres are involved in controlling the cell cycle, cell replication and aging, nucleoside analog containing compositions of the present invention can prevent or control uncontrolled cell growth and the immortality of tumor cells. The compositions of the present invention find particular utility in the treatment of cell proliferative disorders, and in particular human tumors characterized as having telomeres maintained or elongated by telomerase or L1RT.

Thus, in an aspect, the present invention features a method for treatment of a condition associated with telomeres maintained or elongated by telomerase or L1RT, particularly elevated level of telomerase or L1RT activity in a cell. The method involves administering to that cell or a mammal in need of the treatment a composition containing a therapeutically effective amount of at least one nucleoside analog that is an acyclic, anti-telomerase, anti-L1RT and antineoplastic agent. The level of telomerase activity or L1RT activity in a cell can be measured as described, for example, in the Applicant's U.S. Patent Application 60/655,105, entitled "Modulation Of Telomere Length In Telomerase Positive Cells For Cancer Therapy" filed Mar. 25, 2005 and the International Patent Application PCT/US05/001319 entitled "Modulation Of Line-1 Reverse Transcriptase" filed Jan. 18, 2005, which patent applications are incorporated herein by reference. The level of telomerase activity or L1RT activity in a cell may also be measured by any other existing method or equivalent method. By "elevated level" of telomerase activity or L1RT activity, it is meant that the absolute level of telomerase activity or L1RT activity in the particular cell is elevated compared to normal cells in that subject or individual, or compared to normal cells in other subjects or individuals not suffering from the condition. Examples of such conditions include cancerous conditions, or conditions associated with the presence of cells which are not normally present in that individual. Preferably, the compositions contain GCV or ACV or their prodrugs. The use of these compositions (which either directly inhibit the telomerase activity or L1RT activity or indirectly incorporate into telomere and thus prevent telomere's further elongation) should lead to progressive telomere shortening in tumors where telomerase or L1RT is active. Once the telomere length shortens to a critical length, the tumor will go into crisis and eventually die. These inhibitors should have little or no effect on the normal somatic cells because telomerase activity and/or L1RT activity in normal cells is generally low or undetectable.

Interference with telomere elongation or maintenance may either directly result in cell death or may potentiate the effects of chemotherapeutic agents that ultimately kill cells through apoptosis. In particular, the invention provides a method for inhibiting proliferation of telomerase/L1RT expressing cells having potential for continuous increase in cell number by administering the compositions containing the acyclic nucleoside analogs of the present invention. Administration of a nucleoside analog can be achieved by any desired means well known to those of ordinary skill in the art.

In an embodiment of the invention, a method for prevention of a cancer characterized by expression of telomerase or L1RT in cells of a mammal or a subject (e.g. a human) in need thereof is provided. The preventive method involves administration of a therapeutically effective amount of a composition to the mammal. The composition has a telomerase inhibitor or antagonist of the present invention. The inhibitor or antagonist blocks the lengthening of telomeres in telomerase-positive/telomerase-positive cells, thereby inhibiting proliferation of telomerase expressing cells. The inhibitor is an acyclic nucleoside analog or a pharmaceutically acceptable salt of such an analog or a liquid or solid food material that is enriched with the inhibitor or antagonist. The food product can be, for example, a functional food in the form of butter, margarine, biscuits, bread, cake, candy, confectionery, yogurt or another fermented milk product, or cereal suitable for consumption by humans. Alternatively, it can be a nutritional supplement, a nutrient, a pharmaceutical, food, a nutraceutical, a health food and/or a designer food. Periodically, the human is tested for the presence of telomerase positive cells. The use of inhibitor or antagonist may be stopped once the telomerase positive cells are no longer detected in the mammal.

In addition to the therapeutic aspect, the present invention also provides diagnostic methods and kits for detecting pathologically proliferating cells expressing telomerase or L1RT. These and other embodiments of the invention will be described in more detail below.

DETAILED DESCRIPTION OF THE INVENTION

Figure 1:
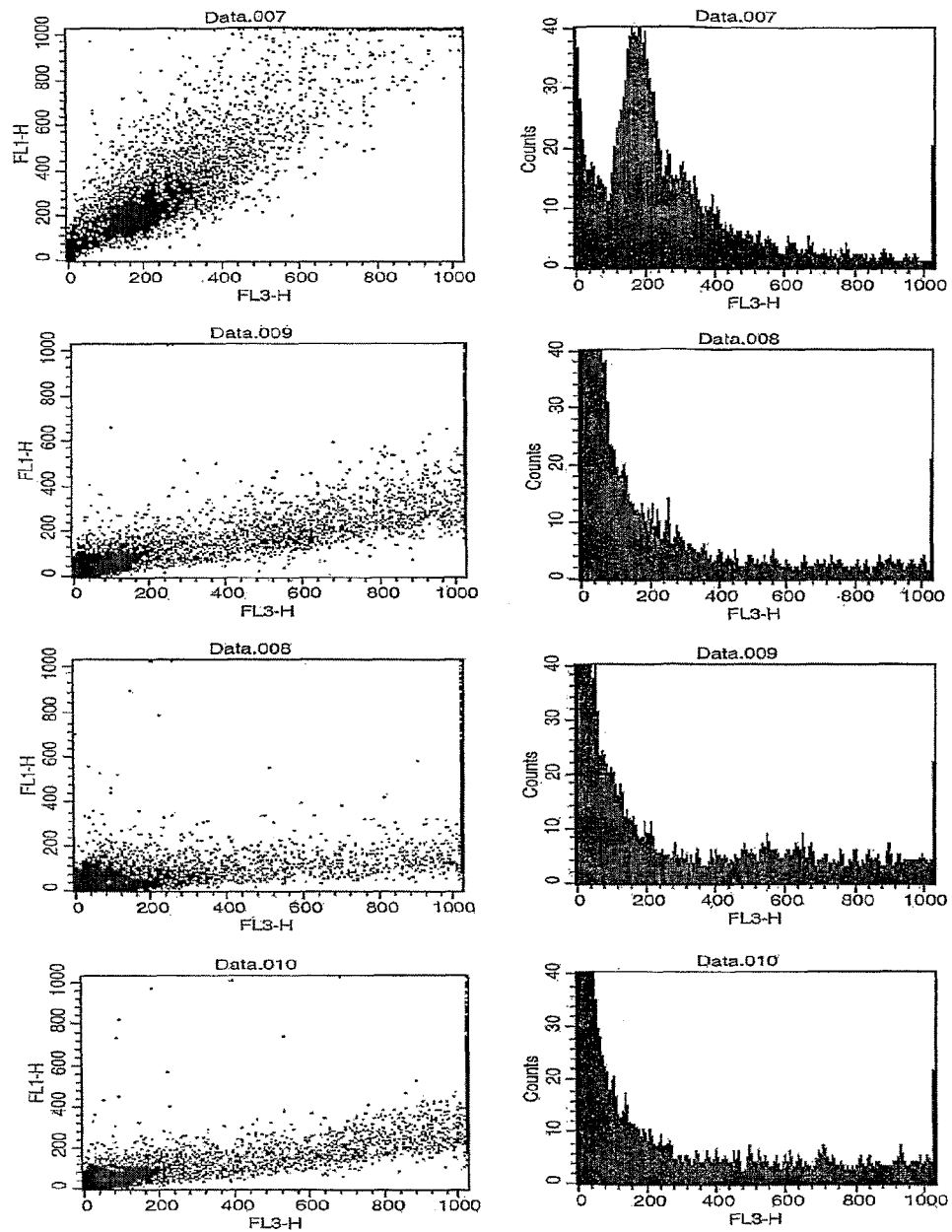
FIG. 1 illustrates flow-FISH data showing decrease in telomere length, massive apoptosis and changes in cell cycle (dot plots—left panels, histogram plots—right panels) in HeLa cells after 10 days of treatment. Data.007—no treatment; Data.008—treatment with 3 µM of ACV; Data.009—treatment with 1.5 µM of GCV; Data.010—treatment with µM 1.5 of PCV. FL1—PNA-FITC, FL3—PI.

The present invention provides compositions and methods involving the use of nucleoside analogs capable of interfering with telomere elongation in cells. In particular, it has been found that certain nucleoside analogs can affect telomere, telomerase and L1RT function in cells at clinically acceptable levels. Specifically, in the context of this invention, the "nucleoside analogs" are compounds with structural similarities to the naturally occurring nucleosides but are limited to those analogs that are acyclic. The acyclic nucleoside analogs contemplated in the present invention are those having a purine (or a pyrimidine) skeleton with a tail portion (e.g., 9-(1,3-dihydroxy-2-propoxymethyl present in guanine) but lacking the hydroxyl cyclic ring (pentose). Examples of the analogs of the present invention include but are not limited to the following: acyclovir, ganciclovir, penciclovir and the corresponding pro-drugs, i.e., valacyclovir, valganciclovir and famciclovir, respectively. Acyclovir[12] acts by mimicking a cellular DNA constituent, guanine. That is the "G" in the AT-CG of DNA. Acyclovir (9-[2(hydromethoxy)-methyl] guanine), although structurally similar to "G," is missing its tail a hydroxyl "cyclic" ring (pentose) and thus it is "acyclic." Ganciclovir[13,14,15] and penciclovir[16,17] are also "acyclic" because they too lack the hydroxyl cyclic ring. In an embodiment of the invention, the tail portion of the acyclic nucleoside analogs of the present invention has at least one hydroxyl group mimicking the 3'- and 5'-hydroxyl groups of the 2'-deoxyribose moiety of nucleosides. The acyclic nucleoside analogs of the present invention have been found to exhibit antitelomerase and antineoplastic properties with clinically acceptable degree of toxicity. The acyclic nucleoside analogs acyclovir, ganciclovir, penciclovir and the corresponding pro-drugs, i.e., valacyclovir, valganciclovir and famciclovir, are all approved for clinical use as antiviral drugs. Their chemical structures and dosage regimens for combating viral infections are well known to one skilled in the art.

While acyclovir, ganciclovir, penciclovir and the corresponding pro-drugs are well known medicines for the treatment of or relief from Herpes virus or/and CMV infections, their use in therapy of neoplastic diseases is unknown. For example, penciclovir is used on the lips and faces of humans to treat cold sores caused by herpes simplex virus. It is also known in the art that the target enzyme for these nucleoside analogs is the DNA polymerase.

In the present invention it has been shown that the acyclic antiviral agents can also target telomerase or L1RT and affect telomere lengthening (or damage telomeres) in cells of a mammal. It is believed that these agents, once inside a proliferating cell, get phosphorylated (e.g., di- and triphosphate forms) and compete with the natural substrates (e.g., dGTP) of the telomerase reaction. The phosphorylated analogs can inhibit the incorporation of the natural substrates into the growing telomere DNA chain or can themselves become incorporated into DNA thereby interfering with telomerase or L1RT mediated polymerization activity, which eventually leads to termination of chain elongation. In essence, these nucleoside analogs, by termination of chain elongation, damage telomeric DNA, shorten telomeres and cause apoptosis. Damage to telomeres is more detrimental to rapidly growing (e.g., tumor) cells than to normal cells.

The anti-HIV and anti-herpes nucleoside analogs have been reported to be active only after their phosphorylation from the nucleoside to the nucleotide stage. Thus, phosphorylation appears to be a crucial factor for the activity of nucleoside analogs against their targets. In this regard, AZT has been reported to require three consecutive phosphorylations for it to be active against telomerase.

The acyclic nucleoside analogs of the present invention are more potent and selective inhibitors of telomere lengthening than the prior art known antitelomerase nucleoside analogs such as AZT; clinically acceptable doses[18,19,20,21,22] are sufficient for realizing a decrease in telomere length and apoptosis or cell death as compared to the nucleoside analogs such as AZT.

Although not suggesting the advantageous uses made possible by this invention, the previous administration of, for example, GCV for treating CMV (cytomegalovirus) infections in patients with AIDS or other immunodeficiencies means that GCV can be readily administered to cancer patients.

Further, the present use of a number of acyclic nucleoside analogs to HSV and CMV patients, coupled with the ability to use significantly lower doses of these analogs, should speed up regulatory approval for the use of acyclovir, ganciclovir, penciclovir and the corresponding pro-drugs, i.e., valacicalovir, valganciclovir and famciclovir, in the treatment of telomerase and/or L1RT induced and/or mediated cancers.

The present invention also encompasses the use of various animal models. By developing or isolating cell lines that express telomerase one can generate disease models in various laboratory animals. These models may employ the subcutaneous, orthotopic or systemic administration of cells to mimic various disease states. For example, the HeLa cell line can be injected subcutaneously into nude mice to obtain telomerase positive tumors. The resulting tumors should show telomerase activity in telomeric repeat amplification protocol (TRAP) assay. Such animal models provide a useful vehicle for testing the nucleoside analogs individually and in combinations as well.

Determining the effectiveness of a compound in vivo may involve a variety of different criteria including, but are not limited to, survival, tumor regression, arrest or slowing of tumor progression, elimination of tumors and inhibition or prevention of metastasis.

Treatment of animals with a test compound would involve the administration of the compound or composition in an appropriate form to the animal. The pharmaceutical compositions, inhibitory or antagonistic agents of the present invention can be administered in a variety of ways including but not limited to oral, parenteral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

The compositions of the present invention would be important in a number of aspects. They would be important in regimens for the treatment of telomerase/L1RT-related cancers, whether administered alone or in combination with chemo- and/or radiotherapeutic regimens known to one skilled in the art in the treatment of cancer. Alternatively, by simply reducing telomerase or L1RT activity, these compositions will be instrumental in selectively inducing massive apoptosis of cancer cells.

The nucleoside analogs may be administered in a physiologically or pharmaceutically acceptable carrier to a host for treatment of proliferative diseases, etc. Pharmaceutically acceptable carriers are determined in part by the particular composition being administered as well as by the particular method used to administer the composition.

In an aspect of the present invention, methods for preventing or treating disorders caused by the presence of inappropriately or pathologically proliferating cells or immortal cells in mammals are provided. The inappropriately or pathologically proliferating cells or immortal cells exist and reproduce independently of cells' normal regulatory mechanisms. These cells are pathologic because they deviate from normal cells as a result of activity of a cellular element, i.e., telomerase. Of course, the inappropriately proliferating cells as used herein may be benign hyperproliferating cells but, unless stated otherwise, these cells refer to malignant hyperproliferating cells such as cancer cells of all kinds including, for example, osteosarcoma, breast carcinoma, ovarian carcinoma, lung carcinoma, adrenocortical carcinoma or melanoma. In one embodiment of the invention, post-transplant lymphoproliferative disease (PTLD), which is a cancer of the blood, is excluded from the scope of cancers contemplated herein.

In particular, methods for preventing or treating human tumors characterized as expressing telomerase or L1RT are provided. The prevention or treatment of the disorders, according to the present invention, is achieved by the utilization of acyclic nucleoside analogs (inhibitors or antagonists of telomerase or L1RT) of the present invention. The inhibitor(s) or antagonist(s) used in the present invention are those acyclic nucleoside analogs that directly or indirectly interact with telomerase and L1RT to inhibit their activity and/or those that get incorporated into telomere and thus prevent telomere from further elongation despite the functional telomerase or L1RT thereby inhibiting the growth of cells expressing telomerase or L1RT. Thus, the inhibitors or antagonists of telomerase or L1RT are used for inhibiting the growth of cells. For example, when the inhibitors or antagonists of telomerase or L1RT are administered to a patient, these cause progressive telomere shortening, cell cycle arrest in the cells and/or massive apoptosis of the cells expressing telomerase. In the present invention, the terms "inhibiting the growth" or "inhibition of growth" may also mean reducing or preventing cell division Inhibition of growth of cells expressing telomerase and/or L1RT, according to the present invention, may be about 100% or less but not 0%. For example, the inhibition may be from about 10% to about 100%, preferably at least about 25%, and more preferably at least about 50%, still more preferably at least about 90%, 95% or exactly 100% compared to that of the control cells (control cells express telomerase but are not treated with an inhibitor or antagonist). The inhibition of growth can be measured by any methods known in the art. For example, viable cell number in treated samples can be compared with viable cell number in control samples, determined after incubation with vital stains. In addition, growth inhibition can be measured by assays that can detect reductions in cell proliferation in vitro or in vivo, such as tritiated hydrogen incorporation assays, BdU incorporation assay, MTT assay, changes in ability to form foci, anchorage dependence or losing immortalization, losing tumor specific markers, and/or inability to form or suppress tumors when injected into animal hosts (Dorafshar et al., 2003, J Surg Res., 114:179-186; Yang et al., 2004, Acta Pharmacol Sin., 25:68-75).

The development of a cancerous tumor from a single immortalized cell or few such cells may take several months to years in humans. By practising the present invention, however, cancer can be prevented because the ability of the tumorigenic cells treated with compositions containing one or more acyclic nucleoside analogs lose their proliferative potential before they have had a chance to grow into a tumor. Further, periodic preventative administration of the inhibitors or antagonists to at risk groups in order to stop tumor progression before clinical manifestation of cancer could potentially decrease the rate of new cancer cases significantly.

The nucleoside compounds may be administered either singly or in combinations of different analogs and by any routes of administration, including oral administration. The nucleoside analogs ACV, GCV or their L-valil esters valganciclovir (V-GCV) and valacyclovir (V-ACV) are the preferred nucleoside analogs. All of them are commercially available and the formulations are described in a number of patents and publications.

The cells with telomerase and/or L1RT activity should be selectively targeted because these cells depend on telomerase and/or L1RT for elongating or maintaining telomeres and the elongation or maintenance of telomeres requires the interaction of the nuclosides and/or their analogs with telomerase or L1RT. To the extent any specific targeting agent is desired for delivering the analogs to exert anti-cancer effects, the use of targeted PCV or ACV or GCV and/or other analogs are contemplated herein. Accordingly, in some embodiments, pharmaceutical compositions may have the active compound, in this case, PCV, ACV and GCV or a other nucleoside analog, which has been conjugated to a targeting agent (e.g., a peptide) for specific delivery to particular target cells or to nuclear portion within cells.

The dose of a given inhibitor or antagonist of telomerase and L1RT can be determined by one of ordinary skill in the art upon conducting routine experiments. Prior to administration to patients, the efficacy may be shown in standard experimental animal models. In this regard any animal model for telomerase induced cancer known in the art can be used (Hahn et al., 1999, Nature Medicine, 5(10):1164-1170; Yeager et al., 1999, Cancer Research, 59(17): 4175-4179). The subject, or patient, to be treated using the methods of the invention is preferably human, and can be a fetus, child, or adult. Other mammals that may be treated can be mice, rats, rabbits, monkeys and pigs.

The inhibitors or antagonists can be used alone or in combination with other chemotherapeutics or otherwise. For example, therapy of telomerase induced cancers may be combined with chemo and/or radiotherapy to treat cancers induced by telomerase or some other factors. Examples of chemotherapeutic agents known to one skilled in the art include, but are not limited to, anticancer drugs such as bleomycin, mitomycin, nitrogen mustard, chlorambucil, 5-fluorouracil (5-FU), floxuridine (5-FUdR), methotrexate (MTX), colchicine and diethylstilbestrol (DES). To practice combined therapy, one would simply administer to an animal an inhibitor component of the present invention in combination with another anti-cancer agent (chemo or radiation) in a manner effective to result in their combined anti-cancer actions within the animal or patient. The agents would therefore be provided in amounts effective and for periods of time effective to result in their combined presence in the region of target cells. To achieve this goal, the agents may be administered simultaneously, and in the case of chemotherapeutic agents, either in a single composition or as two distinct compositions using different administration routes. Alternatively, the two treatments may precede, or follow, each other by, e.g., intervals ranging from minutes to hours or days. By way of example, and not limitation, the average daily doses of GCV for systemic use may be 100 mg/kg per day for human adults, 50 mg/kg per day for mice and human infants.

Some variation in dosage may occur depending on the condition of the subject being treated. The physician responsible for administration will be able to determine the appropriate dose for the individual patient and may depend on multiple factors, such as, the age, condition, file history, etc., of the patient in question.

Accordingly, the methods of the invention can be used in therapeutic applications for conditions and diseases associated with telomerase induced pathological proliferation of cells. Diseases that would benefit from the therapeutic applications of this invention include all diseases characterized by cell hyperproliferation including, for example, solid tumors and leukemias, and non-cancer conditions. It is further contemplated that the method of the invention can be used to inhibit the growth of cancer cells not only in an in vivo context but also in an ex vivo situation. The method of the invention is particularly useful for inhibiting the growth of pathologically proliferating human cells ex vivo, including, but not limited to, human cancer cells—osteosarcoma, breast carcinoma, ovarian carcinoma, lung carcinoma, adrenocortical carcinoma or melanoma.

The present invention provides methods and kits for identifying inappropriately, pathologically or abnormally proliferating cells due to the expression of telomerase or L1RT in the cells. The methods can be used as a screening method that aids in diagnosing the presence of a cancerous cell or tumor in a patient by determining the presence (and/or level) of expression of telomerase or L1RT in tissues from the patient, the presence of telomerase or L1RT expression at elevated levels is being indicative of cancer cells or pathological cell proliferation in the patient.

For example, cancerous tumor samples can be diagnosed by their inability to proliferate in the presence of the acylic nucleoside analogs of the present invention. The diagnosis may further involve the detection of telomerase specific mRNA expression measured by a variety of methods including, but not limited to, hybridization using nucleic acid, Northern blotting, in situ hybridization, RNA microarrays, RNA protection assay, RT-PCR, real time RT-PCR, or the presence of telomerase catalytic subunit encoded protein measured by variety of methods including, but not limited to, Western blotting, immunoprecipitation or immunohistochemistry, or enzymatic activity of telomerase (TRAP assay and its modifications[4,26,27]).

In a preferred embodiment, nucleic acid probes directed against telomerase catalytic subunit RNA can be used to detect presence and/or increases in telomerase catalytic subunit RNA mRNA levels in tissues undergoing rapid proliferation, such as primary cancer cells, including human osteosarcoma, breast carcinoma, ovarian carcinoma, lung carcinoma, adrenocortical carcinoma or melanoma. Thus, the present invention provides methods of using nucleic acid probes that are complementary to a subsequence of an telomerase to detect and identify pathologically proliferating cells, including cancer cells. For example, the method for identifying a pathologically proliferating cell may involve using a nucleic acid probe directed against hTERT mRNA or L1RT mRNA to compare the level of expression of hTERT mRNA or L1RT mRNA in a test cell with the level of expression of hTERT mRNA or L1RT mRNA in a control cell. A test cell is identified as a pathologically proliferating, cell when the level of hTERT or L1RT expression is observed as in the control cell. The nucleic acid probe used in the method of the invention, however, may also be substantially complementary to an hTERT mRNA or L1RT mRNA sequence of human, mouse or other mammal.

It will be apparent to one of ordinary skill in the art that substitutions may be made in the nucleic acid probe which will not affect the ability of the probe to effectively detect the hTERT mRNA or L1RT mRNA in pathologically proliferating cells (e.g., cancer cells) and thus, such substitutions are within the scope of the present invention. The nucleic acid probe used in the method of the present invention can be a DNA probe, or a modified probe such a peptide nucleic acid probe, a phosphorothioate probe, or a 2'-O methyl probe. The length of the nucleic acid probe may be from about 8 or 10 to 50 nucleotides, preferably from about 15 to 25 nucleotides in length. The method of the invention can be readily performed in a cell extract, cultured cell, or tissue sample from a human, a mammal, or other vertebrate.

The methods of the present invention are useful for detecting the inappropriately, pathologically or abnormally proliferating cells due to the expression of telomerase in the cells in vitro, in cell cultures, and in human cells and tissues, such as solid tumors and cancers (e.g., human osteosarcoma, breast carcinoma, ovarian carcinoma, lung carcinoma, adrenocortical carcinoma or melanoma).

The present invention also provides kits for detecting and/ or inhibiting hyperproliferating cells or cancer cells. The kit can have PCV, ACV, GCV, valganciclovir valacyclovir or other acyclic nucleoside analogs and/or have a nucleic acid probe that is fully or substantially complementary to a subsequence of an hTERT mRNA or L1RT mRNA.

The pharmaceutical compositions, inhibitory or antagonistic agents of the present invention can be administered in a variety of ways including orally, topically, parenterally e.g. subcutaneously, intraperitoneally, by viral infection, intravascularly, etc. Depending upon the manner of introduction, the compounds may be formulated in a variety of ways. Formulations suitable for oral administration can be liquid solutions. Formulations suitable for parenteral administration (e.g., by intraarticular, intraventricular, intranasal, intravenous, intramuscular, intradermal, intraperitoneal, and subcutaneous routes) include aqueous and non-aqueous, isotonic sterile injection solutions. In the practice of this invention, compositions can be administered, for example, by intravenous infusion, orally, topically, parenterally or intraperitoneally. Oral and parenteral administrations are the preferred methods of administration. Techniques for formulation and administration are routine in the art and further details may be found, for example, in Remington's Pharmaceutical Sciences (2000), Gennaro AR(ed), 20th edition, Maack Publishing Company, Easton, Pa.

Therapeutically effective amount or pharmacologically effective amount are well recognized phrases in the art and refer to that amount of an agent effective to produce the intended pharmacological result. For example, a therapeutically effective amount is an amount sufficient to effect a beneficial therapeutic response in the patient over time (i.e., to treat a disease or condition or ameliorate the symptoms of the disease being treated in the patient). The amount actually administered will be dependent upon the individual to which treatment is to be applied, and will preferably be an optimized amount such that the desired effect is achieved without significant side effects. As described further in detail below, the dose may also be determined by the efficacy of the particular inhibitor or antagonistic agent employed and the condition of the patient, as well as the body weight or surface area of the patient to be treated. The size of the dose also will be determined by the existence, nature, and extent of any adverse side-effects that accompany the administration of, for example, a particular agent, vector or transduced cell type to a particular patient.

Therapeutically effective doses of agent(s) capable of preventing, inhibiting or reducing the incidence of telomerase/ L1RT mediated cancer are readily determinable using data from cell culture assays disclosed herein and/or from in vivo assays using an animal model. The animal model can also be used to estimate appropriate dosage ranges and routes of administration in humans. Experimental animals bearing solid tumors of human origin (or art-accepted animal models) are frequently used to optimize appropriate therapeutic doses prior to translating to a clinical environment. Such models are known to be very reliable in predicting effective anti-cancer strategies. For example, mice bearing solid tumors or art-accepted mouse models are widely used in pre-clinical testing to determine working ranges of therapeutic agents that give beneficial anti-tumor effects with minimal toxicity. Due to the safety already demonstrated in art-accepted models, at least with respect to nucleoside analogs exemplified herein, pre-clinical testing of the present invention will be more of a matter of routine experimentation. In vivo efficacy may be predicted using assays that measure inhibition of tumor formation (progression), tumor regression or metastasis, and the like.

Exemplary in vivo assays of anti-tumor efficacy of ACV, PCV and/or GCV using nude mice subcutaneous (s.c.) tumors grown from the human HeLa cancer cell line (i.e., xenografts bearing mice) as cancer models are described below.

Human cancerous cells needed for in vivo assays may be prepared, for example, as follows: Telomerase positive HeLa human cell line and telomerase negative U-2 OS human cell line are obtained from public sources. Cells are maintained in D-MEM media supplemented with 10% foetal calf serum at 37° C. in a humidified atmosphere of 5% $CO_2$.

For in vivo assay, appropriate host, e.g., nude (nu/nu) mice of about 5-7 weeks old are obtained and maintained in pathogen-free conditions. Approximately, $1\times10^6$ HeLa cells (and/ or U-2 OS cells) contained in 200 µl of serum-free media are delivered to all animals, briefly anaesthetized with Metofane, by subcutaneous (s.c.) injection in flank. Then the mice are divided into experimental group and control group. Appropriate concentrations of ACV, PCV and/or GCV are used for tumor growth progression or regression assays.

In one embodiment, impairment of s.c. tumor growth or time to progression rather than decrease in size of an established tumor (regression) is assessed. In this embodiment, starting from the day zero, mice in the experimental group receive GCV in drinking water ad libitum. Concentration of GCV in water can be 2 mg/ml. Fresh solution of GCV is supplied every 3 days. Mice in the control group receive only drinking water. Tumors are measured every 2-3 days. Mice are sacrificed when tumors exceed 1 $cm^3$. Tumor volume is calculated with formula $4/3\pi r^3$, where r is the radius of the tumor. All mice in the control group should develop tumors and all mice in the experimental group remain tumor free.

In another embodiment, the reagents and methods of the invention can be used to promote tumor regression in vivo in immunocompetent animals carrying pre-established tumors; i.e., the reagents of the invention can be used to treat animals with pre-existing tumors. In this case, $10^6$ mouse hapatoma MH-22 cells or the like are injected subcutaneously in the flank of the C3HA mice to establish tumors. Once tumors are established after tumor cell implantation, the mice in the experimental group are administered with a composition containing Famvir i.g. solution in drinking water ad libitum, and the mice in the control group receive the same composition but without the drug (e.g., distilled water). Tumor growth is monitored every 2-3 days. Famvir contains famciclovir, an orally administered prodrug of the penciclovir. Chemically, famciclovir is known as 2-[2-(2-amino-9H-purin-9-yl)ethyl]-1,3-propanediol diacetate. When Famvir is administered 21-28 days to these tumor bearing animals, retarded tumor growth is observed. Such inhibition of tumor cell growth is not observed in the control group. Few weeks after the start of the treatment, only the animals treated with Famvir show 100% survival.

In another embodiment, in vivo assays that qualify the promotion of apoptosis may also be used. In this embodiment, xenograft bearing animals treated with the therapeutic composition may be examined for the presence of apoptotic foci and compared to untreated control xenograft-bearing animals. The extent to which apoptotic foci are found in the tumors of the treated animals provides an indication of the therapeutic efficacy of the composition.

In designing appropriate doses of agent(s) for the treatment of human telomerase-mediated callers (both early stage tumors and vascularized tumors), one may readily extrapolate from the animal studies described herein in order to arrive at appropriate doses for clinical administration. To achieve this conversion, one would account for the mass of the agents administered per unit mass of the experimental animal and, preferably, account for the differences in the body surface area between the experimental animal and the human patient. All such calculations are well known and routine to those of ordinary skill in the art. Thus, the determination of a therapeutically effective dose is well within the capability of those skilled in the art.

For example, in taking the successful doses of GCV or ACV (V-GCV or V-ACV) in cell culture assays and in the mouse studies, and applying standard calculations based upon mass and surface area, effective doses for use in adult human patients would be between about 1000 mg and about 6000 mgs of GCV or ACV per patient per day, and preferably, between about 500 mgs and about 1000 mgs of V-GCV or V-ACV per patient per day. Accordingly, using this information, it is contemplated herein that low doses of therapeutic agents (e.g., acyclovir, ganciclovir, penciclovir and the corresponding pro-drugs, i.e., valacicalovir, valganciclovir and famciclovir) for human administration may be about 1, 5, 10, 20, 25 or about 30 mgs or so per patient per day; and useful high doses of therapeutic agent for human administration may be about 250, 300, 400, 450, 500 or about 600 mgs or so per patient per day. Useful intermediate doses may be in the range from about 40 to about 200 mgs or so per patient.

Notwithstanding these stated ranges, it will be understood that, given the parameters and detailed guidance presented herein, further variations in the active or optimal ranges will be encompassed within the present invention. The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 1-500 mgs, and preferably, between about 10-100 mgs of the inhibitor or antagonist of telomerase or therapeutic cocktail containing such, about ~4 times within about a 60 days period. For example, doses would be given on about day 1, day 3 or 4 and day 6 or 7. Administration can be accomplished via single or divided doses taken orally or, for example, by administration to the site of a solid tumor directly or in a slow release formulation. The physician responsible for administration will, in light of the present disclosure, be able to determine the appropriate dose for the individual subject, the form and route of administration. Such optimization and adjustment are routinely carried out in the art and by no means reflect an undue amount of experimentation. In administering the particular doses themselves, one would preferably provide a pharmaceutically acceptable composition according to regulatory standards of sterility, pyrogenicity, purity and general safety to the human patient systemically. Physical examination, tumor measurements, and laboratory tests should, of course, be performed before treatment and at intervals up to one to few months after the treatment and one skilled in the art would know how to conduct such routine procedures. Clinical responses may be defined by any acceptable measure. For example, a complete response may be defined by the disappearance of all measurable tumors within a given period after treatment.

WORKING EXAMPLES

The following working examples are provided to demonstrate preferred embodiments of the invention, but of course, should not be construed as in any way limiting the scope of the present invention. The examples below were carried out using conventional techniques that are well known and routine to those of skill in the art, except where otherwise described in detail. Further, it should be appreciated by those of skill in the art that the techniques disclosed in the examples represent techniques found by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Induction of telomere shortening, G2 arrest and apoptosis in telomerase positive cancer cells have been carried out as described below.

Both telomerase positive (HeLa) telomerase negative (U-2 OS) cell lines were used. Appropriate assays were performed to detect and confirm telomerase/L1RT specific activity in these cells.

Figure 2:
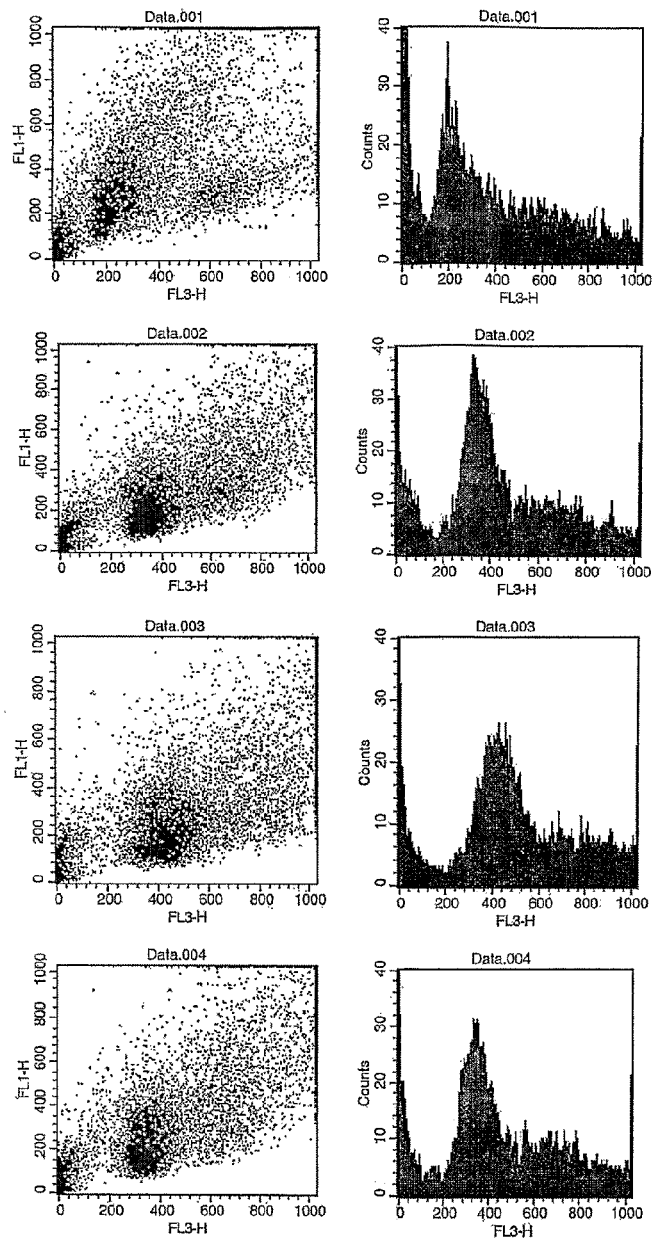
FIG. 2 illustrates flow-FISH data showing decrease in telomere length, massive apoptosis and changes in cell cycle (dot plots—left panels, histogram plots—right panels) in U-2 OS cells after 10 days of treatment. Data.001—no treatment; Data.002—treatment with 3 µM of ACV; Data.003—treatment with 1.5 µM of GCV; Data.004—treatment with 1.5 µM of PCV. FL1—PNA-FITC, FL3—PI.
Figure 3:
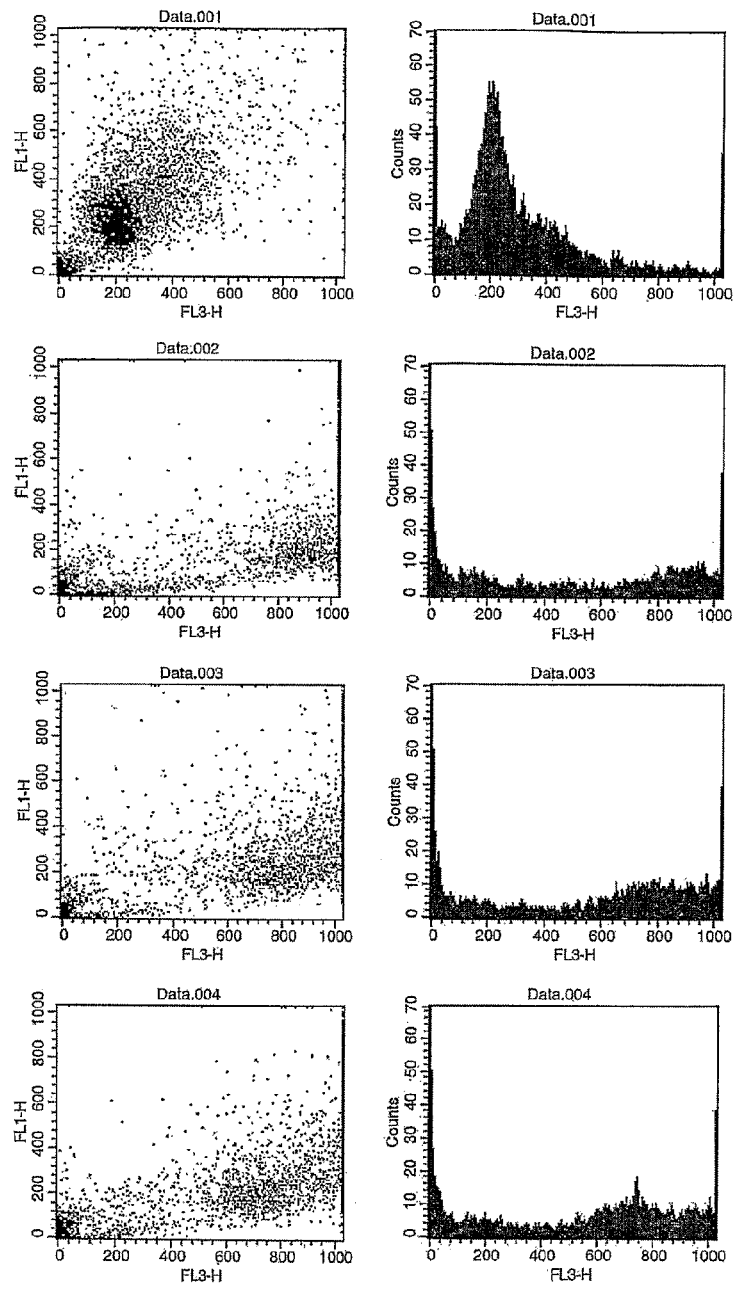
FIG. 3 illustrates flow-FISH data showing decrease in telomere length, massive apoptosis and changes in cell cycle (dot plots—left panels, histogram plots—right panels) in U-2 OS cells after 14 days of treatment. Data.001—no treatment; Data.002—treatment with 3 µM of ACV; Data.003—treatment with 1.5 µM of GCV; Data.004—treatment with 1.5 µM of PCV. FL1—PNA-FITC, FL3—PI.

The cell lines were treated with therapeutic concentrations of ACV (3.0 µM), GCV (1.5 µM) or PCV (1.5 µM) to demonstrate that telomeric DNA synthesis could be inhibited within the cells, and thereby induce telomere shortening. Telomere length in ACV, GCV and PCV treated and untreated cell lines was measured by flow cytometry with a telomere-specific peptide nucleic acid (PNA) probe[23,24]. To determine cell cycle distribution, cells were stained with propidium iodide (PI)[23]. After 10 and 14 days of treatments, both cell lines demonstrated telomere shortening, massive apoptosis and G2 arrest (FIGS. 1, 2 and 3).

To demonstrate changes in cell cycle distribution, HeLa and U-2 OS cells were treated with ACV, GCV or PCV for 14 days stained with PI, and analyzed by flow cytometry simultaneously. Results show G2 arrest of cell cycle. It is important to note that changes were rapid and could be detected after only few days of ACV treatment.

The U-2 OS (osteosarcoma) and HeLa (uterine cervix) cell lines used in this study were obtained from American Type Culture Collection (Rockville, Md.). Cells were cultured in D-MEM media supplemented with 10% fetal calf serum at 37° C. in a humidified atmosphere of 5% $CO_2$. For treatment of the cells with ACV, the media was supplemented with 3 µM of acyclovir (acyclovir, TEVA Pharm. Ind. Ltd, Israel). For treatment of the cells with GCV, the media was supplemented with 1.5 µM of GCV (Cymevene, Hoffman-La Roche). For treatment of the cells with PCV, the media was supplemented with 1.5 µM of PCV (penciclovir, Merck & Co.).

Real time TRAP assay was performed as described (Wege et al., SYBR Green real-time telomeric repeat amplification protocol for the rapid quantification of telomerase activity. *Nucleic Acids Res.* 2003; 31(2):E3-3).

For telomere length measurement by flow cytometry, cells were stained with telomere specific FITC conjugated $(C_3TA_2)_3$ PNA (Applied Biosystems) probe and contrastained with 0.06 µg/ml PI as described by Rufer et al., 1998, Telomere length dynamics in human lymphocyte subpopulations were measured by flow cytometry, *Nat. Biotechnol.* 16, 743-747.

Thus, it has been demonstrated herein that the nucleoside analogs ACV GCV and PCV clearly cause decrease in telomere lengths. Useful inhibitory compounds are not believed to be limited in any way to the specific compounds or nucleotide analogs and derivatives specifically exemplified above. In fact, it may prove to be the case that the most useful pharmacological compounds designed and synthesized in light of this disclosure will be second generation derivatives or further-chemically-modified acyclic nucleoside analogs.

CITED REFERENCES

The references numbered 1-26 below are cited in the above description (with the corresponding superscript numbers) and as such one skilled in the art would match the references to the appropriate superscript numbers in the text above.
1. Olovnikov, A. M. Principle of marginotomy in template synthesis of polynucleotides. *Dokl. Akad. Nauk SSSR* 201, 1496-1499 (1971).
2. Allshire, R. C., Dempster, M., Hastie, N. D. Human telomeres contain at least three types of G-rich repeat distributed non-randomly. *Nucleic Acids Res.* 17, 4611-4627 (1989).
3. Greider, C. W., Blackburn, E. H. Identification of a specific telomere terminal transferase activity in Tetrabymena extracts. *Cell* 43, 405-413 (1985).
4. Morin G B. The human telomere terminal transferase enzyme is a ribonucleoprotein that synthesizes TTAGGG repeats. Cell. 1989 Nov. 3; 59(3):521-9.
5. Kim, N. W., Piatyszek, M. A., Prowse, K. R., Harley, C. B., West, M. D. Specific association of human telomerase activity with immortal cells and cancer. *Science* 266, 2011-2015 (1994).
6. Harley, C. B., Futcher, A. B., Greider, C. W. Telomeres shorten during ageing of human fibroblasts. *Nature* 34, 458-460 (1990).
7. Bryan, T. M., Englezou, A., Dalla-Pozza, L., Dunham, M. A., Reddel, R. R. Evidence for an alternative mechanism for maintaining telomere length in human tumors and tumor-derived cell lines. *Nat. Med.* 3, 1271-1274 (1997).
8. Reddel, R. R., Bryan, T. M., Colgin, L. M., Perrem, K. T., Yeager, T. R. Alternative lengthening of telomeres in human cells. *Radiat. Res.* 155, 194-200 (2001).
9. Wright, W. E., Piatyszek, M. A., Rainey, W. E., Byrd, W., Shay, J. W. Telomerase activity in human geiniline and embryonic tissues and cells. *Dev. Genet.* 18, 173-179 (1996).
10. Greider C W Mammalian telomere dynamics: healing, fragmentation shortening and stabilization. *Curr Opin Genet Dev.* 1994; 4(2):203-11.
11. Hahn, W. C. et al. Inhibition of telomerase limits the growth of human cancer cells. *Nat. Med.* 5, 1164-1170 (1999).
12. Elion, G. B.; Furman, P. A.; Fyfe, J. A.; de Miranda, P.; Beauchamp, L.; Schaeffer, H. J. Selectivity of Action of an Antiherpetic Agent, 9-(2-Hydroxyethoxymethyl)guanine. *Proc. Natl. Acad. Sci. U.S.A.* 1977, 74, 5716-5720.
13. Martin, J. C.; Dvorak, C. A.; Smee, D. F.; Matthews, T. R.; Julien, P. H.; Verheyden, J. P. H. 9-[(1,3-Dihydroxy-2-propyloxy)methyl]guanine: A New Potent and Selective Antiherpes Agent. *J. Med. Chenz.* 1983, 26, 759-761.
14. Smee, D. F.; Martin, J. C.; Verheyden, J. P. H.; Matthews, T. R. Antiherpesvirus Activity of the Acyclic Nucleosides 9-(1,3-Dihydroxy-2-propoxymethyl)guanine. *Antimicrob. Agents Chemother.* 1983, 23, 676-682.
15. Field, E. K.; Davies, M. E.; DeWitt, C.; Perry, H. C.; Liou, R.; Germershausen, J.; Karkas, J. D.; Ashton, W. T.; Johnston, D. B.; Tolman, R. L. 9-([2-Hydroxy-1-(hydroxymethyl)ethoxy]methyl)guanine: A Selective Inhibitor of Herpes Group Virus Replication. *Proc. Natl. Acad. Sci. U.S.A.* 1983, 80, 4139-4143.
16. Hamden, M. R.; Jarvest, R. L.; Bacon, T. H.; Boyd, M. R. Synthesis and Antiviral Activity of 9-[4-Hydroxy-3-(hydroxymethyl)but-1-yl]purines. *J. Med. Chem.* 1987, 30, 1636-1643
17. Vere Hodge, R. A.; Perkins, R. M. Mode of Action of 9-(4-Hydroxy-3-hydroxymethylbut-1-yl)guanine (BRL 39123) against Herpes Simplex Virus in MRC-5 Cells. *Antimicrob. Agents Chemother.* 1989, 33, 223-229
18. de Miranda P, Whitley R J, Blum M R, Keeney R E, Barton N, Cocchetto D M, Good S, Hemstreet G P 3rd, Kirk L E, Page D A, Elion G B. Acyclovir kinetics after intravenous infusion. *Clin Pharmacol Ther.* 1979; 26(6):718-28.
19. Van Dyke R B, Connor J D, Wyborny C, Hintz M, Keeney R E. Pharmacokinetics of orally administered acyclovir in patients with herpes progenitalis. *Am J Med* 1982; 73(1A): 172-5.
20. Lycke J, Malmestrom C, Stahle L. Acyclovir levels in serum and cerebrospinal fluid after oral administration of valacyclovir. Antimicrob Agents Chemother. 2003; 47(8): 2438-41.
21. Piketty C, Bardin C, Gilquin J, Gairard A, Kazatchkine M D, Chast F. Monitoring plasma levels of ganciclovir in AIDS patients receiving oral ganciclovir as maintenance therapy for CMV retinitis. *Clin Microbial Infect.* 2000; 6(3):117-20.
22. Brown F, Banken L, Saywell K, Arum I. Pharmacokinetics of valganciclovir and ganciclovir following multiple oral dosages of valganciclovir in HIV- and CMV-seropositive volunteers. *Clin Pharmacolcinet.* 1999; 37(2):167-76.
23. Rufer, N., Dragowska, W., Thornbury G., Roosnek, E., Lansdorp P. M. Telomere length dynamics in human lymphocyte subpopulations measured by flow cytometry. *Nat. Biotechnol.* 16, 743-747 (1998).
24. Hultdin, M. et al Telomere analysis by fluorescence in situ hybridization and flow cytometry. *Nucleic Acids Res.* 26, 3651-3656 (1998).

25. TRAP-ELISA A. K. Velin, A. Herder, K. J. Johansson et al., Telomerase is not activated in human hyperplastic and adenomatous parathyroid tissue. *Eur J Endocrinol* 145 (2001), pp. 161-164.

26. real time TRAP (Wege et al., SYBR Green real-time telomeric repeat amplification protocol for the rapid quantification of telomerase activity. *Nucleic Acids Res.* 2003; 31(2):E3-3).

All publications, patents and patent applications mentioned in the specification are indicative of the level of those skilled in the art to which this invention pertains. All publications, patents and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

The invention claimed is:

1. A method for treating a cancer in a mammal or a human, the method comprising administering to the mammal or human in need thereof a therapeutically effective amount of a composition comprising one or more acyclic nucleoside analogs, or a pharmaceutically acceptable salt thereof as the only active compounds in the composition for modulation, suppression or inhibition of lengthening of telomeres, wherein the composition induces progressive telomere shortening, $G_2$ phase arrest, chromosomal abnormalities and eventual cell death without regard to telomerase mediated telomere lengthening mechanism or an alternative mechanism of telomere lengthening in cells of the cancer.

2. The method of claim 1, wherein said nucleoside analogs are selected from the group consisting of: acyclovir, ganciclovir and penciclovir or a prodrug thereof.

3. The method of claim 1, wherein the cancer is osteosarcoma, breast carcinoma, ovarian carcinoma, lung carcinoma, adrenocortical carcinoma or melanoma.

4. The method of claim 1, wherein the composition is administered orally, parenterally, subcutaneously, intramuscularly or intravascularly.

5. The method of claim 2, wherein a composition comprising two or more said nucleoside analogs are administered.

6. The method of claim 1, wherein the one of said nucleoside analogs administered is from about 10 mg/kg of body weight to about 150 mg/kg of body weight per day.

7. The method of claim 1, wherein said composition is administered in combination with radiation treatment and/or non-nucleoside chemotherapeutic agent.

8. A method of treating an individual suffering from a cancer comprising administering to the individual in need thereof a therapeutically effective amount of a composition comprising an inhibitor or antagonist of a reverse transcriptase only as the active compound in the composition, wherein the reverse transcriptase is encoded by L-I (LINE-I) retrotransposon or telomerase reverse transcriptase (TERT) and which is involved in said lengthening of telomeres in cells of the cancer, wherein the composition induces progressive telomere shortening, $G_2$ phase arrest, chromosomal abnormalities and eventual cell death in said cells without regard to telomerase mediated telomere lengthening mechanism or an alternative mechanism of telomere lengthening in said cells, wherein the inhibitor or antagonist is an acyclic nucleoside analog selected from the group consisting of: acyclovir, ganciclovir and penciclovir or a prodrug thereof.

9. The method of claim 8, wherein the cancer does not include post-transplant lymphoproliferative disease.

10. The method of claim 9, wherein the cancer is osteosarcoma, breast carcinoma, ovarian carcinoma, lung carcinoma, adrenocortical carcinoma or melanoma.

11. The method of claim 10, wherein the composition is administered orally, parenterally, subcutaneously, intramuscularly, intravascularly or topically.

12. A method for treating a cancer in a human, wherein the cancer is due to cells showing telomerase mediated lengthening of telomeres or alternative lengthening of telomeres induced by L-I (LINE-I) retrotransposon encoded reverse transcriptase in said cells of the human, the method comprising administering a therapeutically effective amount of a composition comprising one or more acyclic nucleoside analogs, or a pharmaceutically acceptable salts thereof, as the only active compounds in the composition for modulation, suppression or inhibition of lengthening of telomeres to the human suffering from the cancer, wherein the composition induces progressive telomere shortening, $G_2$ phase arrest, chromosomal abnormalities and eventual cell death in said cells without regard to telomerase mediated telomere lengthening mechanism or an alternative mechanism of telomere lengthening in said cells, wherein said nucleoside analogs are selected from the group consisting of: acyclovir, ganciclovir and penciclovir or a prodrug thereof.

13. The method of claim 12, wherein the cancer does not include post-transplant lymphoproliferative disease.

14. The method of claim 13, wherein the one of said nucleoside analogs administered is from about 100 mg/kg of body weight to about 500 mg/kg of body weight per day.

15. The method of claim 12, wherein the composition comprises acyclovir or a prodrug thereof.

16. The method of claim 12, wherein the composition comprises ganciclovir a prodrug thereof.

17. The method of claim 12, wherein the composition comprises penciclovir or a prodrug thereof.

18. The method of claim 12, wherein the cancer is osteosarcoma, breast carcinoma, ovarian carcinoma, lung carcinoma, adrenocortical carcinoma or melanoma.

19. The method of claim 18, wherein a composition comprising two or more said nucleoside analogs are administered.

20. The method of claim 18, wherein said composition is administered in combination with radiation treatment and/or non-nucleoside chemotherapeutic agent.

* * * * *